United States Patent
Kelson et al.

(10) Patent No.: US 12,186,412 B2
(45) Date of Patent: *Jan. 7, 2025

(54) POLYMER COATINGS FOR BRACHYTHERAPY DEVICES

(71) Applicant: ALPHA TAU MEDICAL LTD., Jerusalem (IL)

(72) Inventors: Itzhak Kelson, Tel Aviv (IL); Yona Keisari, Ramat Gan (IL); Michael Schmidt, Kfar Saba (IL); Avia Berkowitz, Modiin (IL)

(73) Assignee: ALPHA TAU MEDICAL LTD., Jerusalem (IL)

( * ) Notice: Subject to any disclaimer, the term of this patent is extended or adjusted under 35 U.S.C. 154(b) by 0 days.

This patent is subject to a terminal disclaimer.

(21) Appl. No.: 17/948,280

(22) Filed: Sep. 20, 2022

(65) Prior Publication Data

US 2023/0014526 A1    Jan. 19, 2023

Related U.S. Application Data

(63) Continuation of application No. 16/610,507, filed as application No. PCT/IB2018/053213 on May 9, 2018, now Pat. No. 11,529,432.

(Continued)

(51) Int. Cl.
*A61K 51/12* (2006.01)
*A61K 51/06* (2006.01)
(Continued)

(52) U.S. Cl.
CPC .......... *A61K 51/1282* (2013.01); *A61K 51/06* (2013.01); *A61L 31/10* (2013.01);
(Continued)

(58) Field of Classification Search
None
See application file for complete search history.

(56) References Cited

U.S. PATENT DOCUMENTS 6,254,552 B1 * 7/2001 Lewis ................ A61K 51/1282
600/3
6,589,502 B1 * 7/2003 Coniglione .......... A61N 5/1027
600/7

(Continued)

FOREIGN PATENT DOCUMENTS

CN    101259290 A    9/2008
EP    1426063 A2    6/2004

(Continued)

OTHER PUBLICATIONS

Perry, R. and Snoddy, R. , "A Method for Testing the Diffusion Coefficient of Polymer Films" Prepared for Presentation at the 1996 AARST International Radon Symposium, Sep. 29-Oct. 2, 1996. Haines City, FL https://web.archive.org/web/20100917120623/https://aarst.org/proceedings/1996/1996_2 (Year: 1996).*

(Continued)

*Primary Examiner* — Christine H Matthews
*Assistant Examiner* — Marc D. Honrath
(74) *Attorney, Agent, or Firm* — MEITAR PATENTS LTD.

(57) ABSTRACT

An apparatus includes a support, including an outer surface and configured for insertion into a body of a subject. The apparatus further includes multiple atoms of a radionuclide, which radioactively decays to produce a daughter radionuclide, coupled to the outer surface, and a layer of a polymer, which covers the atoms so as to protect the atoms from being washed away, yet allows diffusion of the daughter radionuclide through the layer. Other embodiments are also described.

20 Claims, 2 Drawing Sheets

Related U.S. Application Data

(60) Provisional application No. 62/504,800, filed on May 11, 2017.

(51) Int. Cl.
 *A61L 31/10* (2006.01)
 *A61N 5/10* (2006.01)

(52) U.S. Cl.
 CPC ........ *A61N 5/1007* (2013.01); *A61L 2420/08* (2013.01); *A61N 2005/1025* (2013.01)

(56) References Cited

U.S. PATENT DOCUMENTS

| | | | | |
|---|---|---|---|---|
| 6,638,205 | B1 * | 10/2003 | Chan | A61N 5/1001 29/458 |
| 11,969,485 | B2 * | 4/2024 | Kelson | A61P 35/00 |
| 2003/0206857 | A1 | 11/2003 | Larsen et al. | |
| 2009/0136422 | A1 * | 5/2009 | Kelson | A61P 35/00 424/1.73 |
| 2012/0123189 | A1 | 5/2012 | Ribbing et al. | |
| 2019/0352459 | A1 | 11/2019 | Axelsson et al. | |

FOREIGN PATENT DOCUMENTS

| | | | | |
|---|---|---|---|---|
| WO | 02078785 | A2 | 10/2002 | |
| WO | WO-2004045549 | A2 * | 6/2004 | ......... A61K 47/6957 |
| WO | 2006043083 | A2 | 4/2006 | |
| WO | 2015057530 | A2 | 4/2015 | |
| WO | 2015142316 | A1 | 9/2015 | |

OTHER PUBLICATIONS

KR Application # 1020197033304 Office Action dated Nov. 16, 2022.
JP Application # 2020551517 Office Action dated Aug. 16, 2023.
CN Application # 2019800233036 Office Action dated Oct. 10, 2023.
U.S. Appl. No. 17/549,929 Office Action dated Aug. 24, 2023.
JP Application # 2020-551517 Office Action dated Nov. 30, 2022.
EP Application # 18797701.2 Office Action dated Oct. 5, 2022.
KR Application # 1020207030889 Office Action dated Nov. 23, 2023.
JP Application # 2023017195 Office Action dated Dec. 5, 2023.
EP Application # 19781797.6 Office Action dated Jan. 25, 2024.
IN Application # 202047044711 Hearing Notice dated Jan. 25, 2024.
U.S. Appl. No. 16/979,543 Office Action dated Nov. 21, 2024.
U.S. Appl. No. 16/979,543 Office Action dated Dec. 21, 2024.
International Application # PCT/IB2024/054121 Search Report dated Aug. 20, 2024.
EP Application # 21905935.9 Search Report dated Sep. 30, 2024.
Wu et al., "Radioactive polymeric nanoparticles for biomedical application," Drug Delivery, vol. 27, No. 1, pp. 1544-1561, year 2020.
Yi et al., "Core-shell Au@MnO2 nanoparticles for enhanced radiotherapy via improving the tumor oxygenation," vol. 9, No. 11, pp. 3267-3278, year 2016.

* cited by examiner

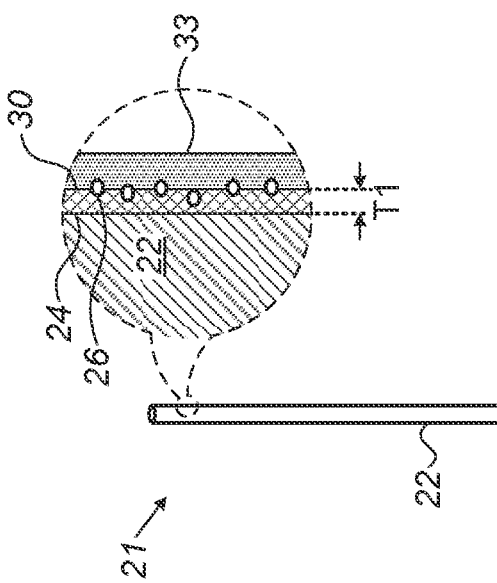
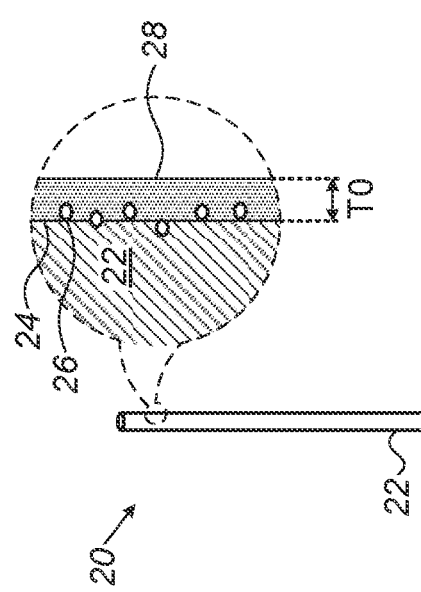
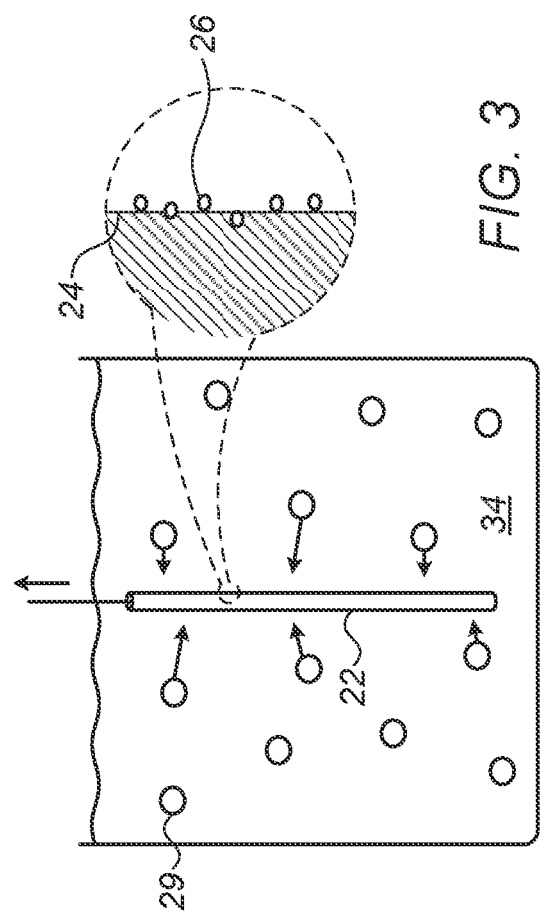

POLYMER COATINGS FOR BRACHYTHERAPY DEVICES

CROSS-REFERENCE TO RELATED APPLICATIONS

The present application is a continuation of U.S. application Ser. No. 16/610,507, which was filed on Nov. 3, 2019 in the national phase of International Application PCT/IB2018/053213, which was filed on May 9, 2018, and claims the benefit of U.S. Provisional Application 62/504,800, filed on May 11, 2017, whose disclosure is incorporated herein by reference.

FIELD OF THE INVENTION

The present invention relates to the field of brachytherapy, such as for the treatment of cancerous tumors.

BACKGROUND

Brachytherapy involves the placement of a radiation source inside the body of a subject, such that the radiation source emits radiation within the body. The emitted radiation may kill cancerous cells in the vicinity of the source.

Arazi, Lior et al., "Treatment of solid tumors by interstitial release of recoiling short-lived alpha emitters," Physics in Medicine & Biology 52.16 (2007): 5025, which is incorporated herein by reference, describes a method utilizing alpha particles to treat solid tumors. Tumors are treated with interstitial radioactive sources which continually release short-lived alpha emitting atoms from their surface. The atoms disperse inside the tumor, delivering a high dose through their alpha decays. This scheme is implemented using thin wire sources impregnated with Ra-224, which release by recoil Rn-220, Po-216 and Pb-212 atoms.

U.S. Pat. No. 8,894,969 to Kelson et al., whose disclosure is incorporated herein by reference, describes a radiotherapy method, comprising positioning a predetermined amount of a radionuclide selected from the group consisting of Radium-223, Radium-224, Radon-219 and Radon-220, in proximity to and/or within a tumor of a subject, for a predetermined time period. The predetermined amount and the predetermined time period are sufficient for the radionuclide to administer a predetermined therapeutic dose of decay chain nuclei and alpha particles into the tumor.

SUMMARY OF THE INVENTION

There is provided, in accordance with some embodiments of the present invention, apparatus that includes a support, including an outer surface and configured for insertion into a body of a subject. The apparatus further includes multiple atoms of a radionuclide, which radioactively decays to produce a daughter radionuclide, coupled to the outer surface, and a layer of a polymer, which is permeable to the daughter radionuclide, that covers the atoms.

In some embodiments, the atoms are disposed on the outer surface.

In some embodiments, the support is cylindrically-shaped.

In some embodiments, the radionuclide is an alpha-emitting radionuclide.

In some embodiments, the radionuclide includes rn isotope of radium selected from the group of isotopes consisting of: Ra-224 and Ra-223.

In some embodiments, the daughter radionuclide is an alpha-emitting daughter radionuclide.

In some embodiments, a thickness of the layer is between 0.1 and 2 microns.

In some embodiments, the thickness is between 0.1 and 1 microns.

In some embodiments, a diffusion coefficient of the daughter radionuclide in the polymer is at least $10^{-11}$ cm$^2$/sec.

In some embodiments, the polymer is selected from the group of polymers consisting of: polypropylene, polycarbonate, polydimethylsiloxane, polyethylene terephthalate, poly(methyl methacrylate), and polysulfone.

In some embodiments,
the layer is an outer layer,
the polymer is a first polymer, and
the apparatus further includes an inner layer of a second polymer, which is permeable to the daughter radionuclide, coating the outer surface, the atoms being coupled to the outer surface by virtue of being coupled to the inner layer.

In some embodiments, an inner-layer thickness of the inner layer is between 0.1 and 7 microns.

In some embodiments, the inner-layer thickness is between 0.1 and 1 microns.

There is further provided, in accordance with some embodiments of the present invention, a method that includes coupling multiple atoms of a radionuclide, which radioactively decays to produce a daughter radionuclide, to an outer surface of a support that is configured for insertion into a body of a subject, and, subsequently to coupling the atoms to the outer surface, covering the atoms with a layer of a polymer that is permeable to the daughter radionuclide.

In some embodiments, covering the atoms includes covering the atoms by withdrawing the support from a solution of the polymer such that the layer of the polymer coats the outer surface.

In some embodiments,
the layer is an outer layer,
the polymer is a first polymer,
the method further includes, prior to coupling the atoms to the outer surface, coating the outer surface with an inner layer of a second polymer, and
coupling the atoms to the outer surface includes coupling the atoms to the outer surface by coupling the atoms to the inner layer.

There is further provided, in accordance with some embodiments of the present invention, a method that includes inserting a radiation source into a body of a subject. The radiation source includes a support, including an outer surface, multiple atoms of a radionuclide, which radioactively decays to produce a daughter radionuclide, coupled to the outer surface, and a layer of a polymer, which is permeable to the daughter radionuclide, that covers the atoms. The method further includes leaving the radiation source within the body of the subject, such that nuclei of the daughter radionuclide diffuse through the layer of the polymer.

In some embodiments, inserting the radiation source into the body of the subject includes inserting the radiation source into a tumor inside the body of the subject.

In some embodiments, inserting the radiation source into the body of the subject includes inserting the radiation source such that the radiation source is within 0.1 mm of a tumor inside the body of the subject.

The present invention will be more fully understood from the following detailed description of embodiments thereof, taken together with the drawings, in which:

BRIEF DESCRIPTION OF THE DRAWINGS

FIGS. 1-2 are schematic illustrations of brachytherapy devices, in accordance with some embodiments of the present invention;

FIG. 3 is a schematic illustration of a dip-coating technique for the manufacture of a brachytherapy device, in accordance with some embodiments of the present invention.

DETAILED DESCRIPTION OF EMBODIMENTS

Overview

Figure 4:
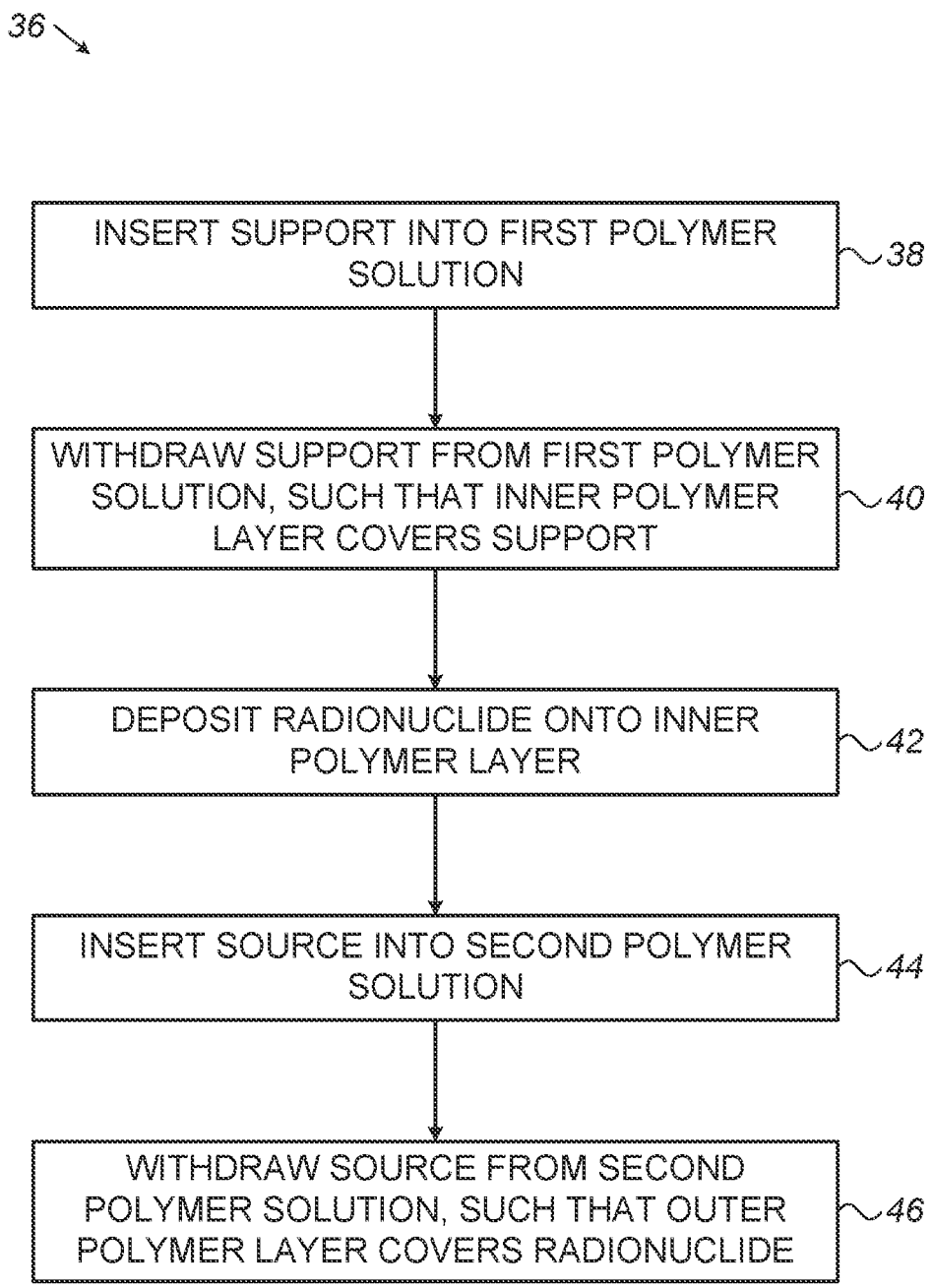
FIG. 4 is a flow diagram for a method for the manufacture of a brachytherapy device, in accordance with some embodiments of the present invention.

In embodiments of the present invention, atoms of an alpha-emitting radionuclide, such as Radium-224 (Ra-224), are deposited onto the surface of a support, such as a wire. The support which, further to having the radionuclide deposited thereon, may be referred to as a "radiation source" or simply as a "source"—is then inserted into a solid tumor within the body of a subject. Subsequently, the radionuclide undergoes a chain of radioactive decay, whereby alpha particles, which kill the cancerous cells of the tumor, are emitted by the radionuclide atoms and by the successive decay-chain nuclei. (Each of these nuclei is referred to herein as the "daughter" of the preceding nucleus in the chain. In general, the terms "atom" and "nucleus" may be used interchangeably herein.) Advantageously, the decay chain nuclei migrate through the tumor by diffusion and/or convection, such that alpha particles may be emitted even at a relatively significant distance from the source.

A challenge, when applying the above-described brachytherapy technique, is that it is generally necessary to cover the radionuclide, such that the radionuclide is not washed away from the source by body fluids before the radionuclide has an opportunity to decay, yet covering the radionuclide may inhibit the desorption of the daughter of the radionuclide from the source. One option, described in the aforementioned U.S. Pat. No. 8,894,969 to Kelson, is to cover the radionuclide with an extremely thin cover, e.g., having a thickness of 5-10 nanometers, which may be penetrated by the daughter nuclei as the daughter nuclei recoil from the source. However, such a cover may be difficult to manufacture.

To address this challenge, embodiments described herein provide a thicker polymer layer (e.g., having a thickness of 0.1-1 microns) that covers the radionuclide, yet allows the daughter nuclei to diffuse therethrough. Such a layer may be applied to the source by dipping the source into a suitable polymer solution, such that the source becomes coated with the polymer. Examples of suitable polymers include polypropylene, polycarbonate, polydimethylsiloxane, polyethylene terephthalate, poly(methyl methacrylate), and polysulfone.

In some embodiments, yet another polymer layer (e.g., having a thickness of 0.1-1 microns) is applied to the surface of the support before the deposition of the radionuclide. An advantage of such embodiments is that even if a daughter nucleus of the radionuclide recoils toward the surface, the daughter nucleus does not become stuck to, or beneath, the surface; rather, the daughter nucleus may diffuse outward through the inner polymer layer, and then continue to diffuse outward through the outer polymer layer. Typically, the inner polymer layer is applied to the support by dipping the support into a suitable polymer solution. Any of the polymers listed above may be used for the inner layer, provided that the selected polymer does not dissolve into the solution that is used for the subsequent coating of the outer polymer layer.

Apparatus Description

Reference is initially made to FIG. 1, which is a schematic illustration of a brachytherapy device 20, in accordance with some embodiments of the present invention.

Brachytherapy device 20 comprises a support 22, which is configured for partial or full insertion into a body of a subject. Support 22 may comprise, for example, a needle, a wire, a rod, a tip of an endoscope, a tip of a laparoscope, or any other suitable probe. Typically, support 22 is cylindrically-shaped; for example, support 22 may comprise a cylindrically-shaped wire, needle, or rod having a diameter of 0.3-1 mm and/or a length of 5-60 mm. Support 22 comprises an outer surface 24.

Brachytherapy device 20 further comprises multiple atoms 26 of a radionuclide, which decays to produce a daughter radionuclide, coupled to outer surface 24. For example, each atom 26 of the radionuclide may be disposed on or slightly beneath outer surface 24. Typically, the density of atoms 26 on outer surface 24 is between $10^{11}$ and $10^{14}$ atoms per square centimeter.

Typically, the radionuclide, the daughter radionuclide, and/or subsequent nuclei in the decay chain are alpha-emitting, in that an alpha particle is emitted upon the decay of any given nucleus. For example, the radionuclide may comprise an isotope of Radium (e.g., Ra-224 or Ra-223), which decays by alpha emission to produce a daughter isotope of Radon (e.g., Rn-220 or Rn-219), which decays by alpha emission to produce an isotope of Polonium (e.g., Po-216 or Po-215), which decays by alpha emission to produce an isotope of Lead (e.g., Pb-212 or Pb-211).

Typically, atoms 26 are generated by the decay of the preceding radionuclides in the decay chain. For example, as described in U.S. Pat. No. 8,894,969 to Kelson et al., atoms of Ra-224 may be generated by spreading a thin layer of acid containing Uranium-232 (U-232) on a metal. The U-232 decays to produce Thorium-228 (Th-228), which in turn decays to produce Ra-224.

Any suitable technique, such as any one or more of the techniques described in the aforementioned '969 patent to Kelson, may be used to couple atoms 26 to support 22. For example, a generating source that generates a flux of the radionuclide may be placed in a vacuum near support 22, such that nuclei recoiling from the generating source traverse the vacuum gap and are collected onto, or implanted in, surface 24. Alternatively, the radionuclide may be electrostatically collected onto support 22, by the application of a suitable negative voltage between the generating source and the support. In such embodiments, to facilitate the electrostatic collection of the radionuclide, support 22 may comprise an electrically-conductive metal, such as titanium. For example, support 22 may comprise an electrically-conducting metallic wire, needle, rod, or probe. Alternatively, support 22 may comprise a non-metallic needle, rod, or probe coated by an electrically-conductive metallic coating that comprises surface 24.

Brachytherapy device 20 further comprises a layer 28 of a polymer, such as polypropylene, polycarbonate, polydimethylsiloxane, polyethylene terephthalate, poly(methyl methacrylate), and/or polysulfone, that coats surface 24 and thus covers atoms 26. The polymer is permeable to the daughter radionuclide, such that the daughter radionuclide may diffuse through layer 28. For example, the diffusion coefficient of the daughter radionuclide in the polymer may be at least $10^{-11}$ cm²/sec. Typically, the thickness T0 of layer 28 is between 0.1 and 2 microns, such as between 0.1 and 1 microns, such that layer 28 is thick enough to protect the radionuclide from being washed away, yet thin enough to allow the diffusion of the daughter radionuclide therethrough. (For ease of illustration, atoms 26 are drawn disproportionately large relative to the thickness of layer 28.)

To treat the subject, at least one device 20 is inserted fully or partially into the body of the subject, typically into, or immediately adjacent to (e.g., within 0.1 mm, such as within 0.05 mm or 0.001 mm, of) the tumor that is to be treated. Subsequently, while the device remains within the body, the radionuclide decays, thus emitting alpha particles into the tumor. Typically, around 50% of the resulting daughter nuclei recoil inward and become stuck to surface 24; the other daughter nuclei, however, recoil outward, into layer 28. Due to the diffusivity of these daughter nuclei, and/or of the subsequent nuclei in the decay chain, within layer 28, at least some (e.g., more than 99%) of these nuclei may diffuse through the polymer layer, and thus desorb from the device and enter the tumor. Thus, for example, the daughter or other descendant nuclei may enter the tumor at a rate of between $10^2$ and $10^5$, such as between $10^3$ and $10^4$, atoms per second per square centimeter. These nuclei then pass through the tumor by diffusion and/or convection, and, while passing through the tumor, undergo further decay. Thus, alpha particles may be emitted even at a significant distance from the source.

In some embodiments, following the radioactive decay of at least some of the radionuclide atoms—e.g., after a predetermined duration of time, and/or in response to monitoring the size of the tumor and/or the fraction of emitted alpha particles the device is removed from the subject. In other embodiments, the device is not removed from the subject.

Reference is now made to FIG. 2, which is a schematic illustration of an alternative brachytherapy device 21, in accordance with some embodiments of the present invention.

Device 21 differs from device 20 in that device 21 comprises two polymer layers: an inner layer 30 of a first polymer that coats outer surface 24, and an outer layer 33 of a second (different) polymer that coats inner layer 30. Atoms 26 are coupled to outer surface 24 by virtue of being coupled to inner layer 30; for example, each atom 26 may be disposed on, or slightly beneath, the outer surface of inner layer 30, such that the atoms are covered by outer layer 33. In general, each of the layers may comprise any suitable polymer, such as polypropylene, polycarbonate, polydimethylsiloxane, polyethylene terephthalate, poly(methyl methacrylate), and/or polysulfone, provided that the two layers are compatible with one another, as further described below following the description of FIG. 4.

Both the first and second polymers are permeable to the daughter radionuclide; for example, the diffusion coefficient of the daughter radionuclide in each of the polymers may be at least $10^{-11}$ cm²/sec. Typically, the thickness T1 of each of the layers is between 0.1 and 2 microns, such as between 0.1 and 1 microns. Atoms 26 may be deposited onto (or into) inner layer 30 using any of the techniques described above. (Given the relative thinness of the inner layer, the inner layer typically does not inhibit the electrostatic collection of the radionuclide.)

Device 21 may be deployed similarly to device 20. An advantage of device 21 is that even if a daughter nucleus of the radionuclide recoils inward, the daughter nucleus may still diffuse outward through inner layer 30 and then through outer layer 33, such that the probability of desorption from device 21 for the daughter nuclei may be close to 100%. (Even if a given nucleus diffuses inward all the way to the outer surface of the support, the nucleus will not adhere to or penetrate the surface.) Hence, a desired dosage of alpha-particle emission may be attained using only half as many radionuclide atoms 26 as would be necessary using device 20. Thus, for example, using device 21, the density of atoms 26 on inner layer 30 may be between $5*10^{10}$ and $5*10^{13}$ atoms per square centimeter.

In general, any suitable technique may be used to apply polymer layer 28 to device 20, or inner layer 30 and outer layer 33 to device 21. One such technique for device 20 is illustrated in FIG. 3, which is a schematic illustration of a dip-coating technique, for the, manufacture of a brachytherapy device, in accordance with some embodiments of the present invention.

As shown in FIG. 3, to manufacture device 20, radionuclide atoms 26 are first deposited onto outer surface 24. Subsequently, the source (i.e., support 22 together with the radionuclide atoms deposited thereon) is dipped into a solution comprising a polymer solute 29 dissolved within a solvent 34. (For ease of illustration, the dissolved particles of the polymer are drawn disproportionately large.) Next, the source is withdrawn from the solution (as indicated by the upward-pointing mow), such that solute 29 is drawn to the source, and hence, layer 28 coats outer surface 24. The desired thickness of layer 28 may be attained by controlling the concentration of the polymer solute and the speed with which the source is withdrawn from the solution.

The dip-coating technique described above may also be used for the manufacture of device 21. In this regard, reference is now made to FIG. 4, which is a flow diagram for a method 36 for the manufacture of device 21, in accordance with some embodiments of the present invention.

Method 36 begins with a first inserting step 38, at which support 22 is inserted into a first polymer solution. Subsequently, at a first withdrawing step 40, the support is withdrawn from the first polymer solution, such that inner layer 30 covers the support. As with layer 28 of device 20, the desired thickness of inner layer 30 may be attained by controlling the concentration of the polymer solute and the speed with which the support is withdrawn from the solution.

Subsequently, at a depositing step 42, the radionuclide is deposited onto (and/or into) inner layer 30. Next, at a second inserting step 44, the source (i.e., the support together with the radionuclide deposited thereon) is inserted into a second polymer solution, the second polymer being different from the first polymer. Finally, at a second withdrawing step 46, the source is withdrawn from the second polymer solution, such that outer layer 33 covers the radionuclide. As with inner layer 30, the desired thickness of the outer layer may be attained by controlling the concentration of the polymer solute and the speed with which the source is withdrawn from the solution.

In general, for layer 28 of device 20, and for outer layer 33 of device 21, solvent 34 may comprise any suitable organic material that does not dissolve the radionuclide. A similar solvent may be used for the inner polymer layer of device 21.

Table 1 lists, by way of example, six different solutions that may be used to form any one of the polymer layers described herein, each row of the table (following the first row) corresponding to a different respective one of these solutions.

TABLE 1

| Solution | Solute | Solvent |
| --- | --- | --- |
| 1 | Polypropylene | Xylene (e.g., heated to ~100 C.) |
| 2 | Polycarbonate | Dichloromethane (DCM) |
| 3 | Polydimethyl siloxane (PDMS) | Hexane (before curing) |
| 4 | Polyethylene terephthalate (PET) | Hexafluoroisopropanol (HFIP) |
| 5 | Poly (methyl methacrylate) | DCM |
| 6 | Polysulfone | DCM |

For device 21, the respective solutions used for the two polymer layers are selected in view of the constraint that the solvent used for the outer polymer layer not dissolve the inner layer. Table 2 lists, by way of example, five different pairs of solutions that may be used, using the numbering system from Table 1 to identify the solutions.

TABLE 2

| Inner Layer | Outer Layer |
| --- | --- |
| Solution 2 | Solution 3 |
| Solution 6 | Solution 3 |
| Solution 4 | Solution 2 |
| Solution 4 | Solution 3 |
| Solution 4 | Solution 6 |

Experimental Results

The inventors prepared a number of experimental brachytherapy devices, using Ra-224 for the radionuclide. Each of these devices was placed into an environment simulating the interior of a human body, such as serum or water at 37° C., or a mouse tumor. For each device, no loss of radium was detected, indicating that the polymer layer covering the radium prevented the radium from washing away. The device was then tested for radon desorption, using alpha spectroscopy.

The paragraphs below describe, in further detail, the preparation of several experimental devices, along with the tests for radon desorption.

(1) Single Polymer Layer

Ra-224 atoms generated by Th-228 decay were electrostatically collected onto four titanium wires, each wire having a diameter of 0.5 mm. The first wire was dipped into a 5% (by weight) polycarbonate solution having DCM as the solvent, and was then withdrawn from the solution at a speed of 8 mm/sec, resulting in a polymer-layer thickness of approximately 0.25 microns. This procedure was then repeated for the second wire with the concentration of the polycarbonate raised to 7.5%, resulting in a polymer-layer thickness of approximately 0.5 microns. The third wire was dipped into a 15% (by weight) PDMS solution having hexane as the solvent, and was then withdrawn at 12 mm/sec, resulting in a polymer-layer thickness of approximately 0.25 microns. This procedure was then repeated for the fourth wire with the concentration of the PDMS raised to 30%, resulting in a polymer-layer thickness of approximately one micron.

The measured radon desorption probability was 50% for the first wire, 48% for the second wire, and 50% for each of the third and fourth wires. (50% is the theoretical maximum for device 20, given that, as described above with reference to FIG. 1, 50% of the radon nuclei recoil backwards into the source.)

(2) Double Polymer Layer

A titanium wire was dipped into a 2% (by weight) solution of PET dissolved in HFIP with a withdrawal speed of 10 mm/sec, resulting in an inner-layer thickness of 0.2 microns. Subsequently, Ra-224 atoms were collected onto the inner layer. Next, the source was dipped into a 3% (by weight) solution of polycarbonate dissolved in DCM with a withdrawal speed of 10 min/sec, resulting in an outer-layer thickness of 0.25 micron. The measured radon desorption probability was 88%, which is only slightly less than the theoretical maximum of 100%.

(It is noted that the thickness of each polymer layer was measured by the Alpha Energy Loss Spectroscopy method, described in Kelson, I. et al., "Recoil implantation of alpha sources for thickness measurement of thin films," Journal of Physics D: Applied Physics 28.1 (1995): 100, which is incorporated herein by reference.)

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. An apparatus, comprising:
a support, comprising an outer surface and configured for insertion into a body of a subject;
multiple atoms of an alpha-emitting radionuclide, coupled to the outer surface, wherein the radionuclide radioactively decays to produce a daughter radionuclide; and
a layer of a polymer having a thickness of at least 0.1 micron, wherein the layer of the polymer covers the multiple atoms of the radionuclide to protect the multiple atoms of the radionuclide from being washed away by body fluids, and further wherein the layer of the polymer allows diffusion of the daughter radionuclide through the layer of the polymer.

2. The apparatus according to claim 1, wherein the multiple atoms of the radionuclide are disposed on the outer surface.

3. The apparatus according to claim 1, wherein the radionuclide comprises an isotope of radium selected from the group of isotopes consisting of: Ra-224 and Ra-223.

4. The apparatus according to claim 1, wherein the daughter radionuclide is an alpha-emitting daughter radionuclide.

5. The apparatus according to claim 1, wherein the thickness of the layer of the polymer is between 0.1 micron and 2 microns.

6. The apparatus according to claim 1, wherein a diffusion coefficient of the daughter radionuclide in the polymer is at least $10^{-11}$ cm$^2$/sec.

7. The apparatus according to claim 1, wherein the polymer is selected from the group of polymers consisting of: polypropylene, polycarbonate, polydimethylsiloxane, polyethylene terephthalate, poly(methyl methacrylate), and polysulfone.

8. A method, comprising:
coupling multiple atoms of an alpha-emitting radionuclide, which radioactively decays to produce a daughter radionuclide, to an outer surface of a support configured for insertion into a body of a subject; and
subsequently to coupling the multiple atoms of the radionuclide to the outer surface, covering the multiple atoms of the radionuclide with a layer of a polymer having a thickness of at least 0.1 micron, wherein the layer of the polymer protects the multiple atoms of the radionuclide from being washed away by body fluids, and further wherein the layer of the polymer allows diffusion of the daughter radionuclide through the layer of the polymer.

9. The method according to claim 8, wherein covering the multiple atoms of the radionuclide comprises covering the multiple atoms of the radionuclide by withdrawing the support from a solution of the polymer such that the layer of the polymer of the polymer coats the outer surface.

10. The method according to claim 8, wherein the radionuclide includes an isotope of radium selected from the group of isotopes consisting of: Ra-224 and Ra-223.

11. The method according to claim 8, wherein the daughter radionuclide is an alpha-emitting daughter radionuclide.

12. The method according to claim 8, wherein the thickness of the layer of the polymer is between 0.1 micron and 2 microns.

13. The method according to claim 8, wherein a diffusion coefficient of the daughter radionuclide in the polymer is at least $10^{-11}$ cm$^2$/sec.

14. The method according to claim 8, wherein the polymer is selected from the group of polymers consisting of: polypropylene, polycarbonate, polydimethylsiloxane, polyethylene terephthalate, poly(methyl methacrylate), and polysulfone.

15. A method, comprising:
inserting a radiation source into a body of a subject, the radiation source comprising:
a support, including an outer surface,
multiple atoms of an alpha-emitting radionuclide coupled to the outer surface of the support, wherein the radionuclide radioactively decays to produce a daughter radionuclide, and
a layer of a polymer having a thickness of at least 0.1 micron, wherein the layer of the polymer covers the multiple atoms of the radionuclide to protect the multiple atoms of the radionuclide from being washed away by body fluids, and further wherein the layer of the polymer allows diffusion of the daughter radionuclide through the layer of the polymer; and
leaving the radiation source within the body of the subject, such that nuclei of the daughter radionuclide diffuse through the layer of the polymer.

16. The method according to claim 15, wherein inserting the radiation source into the body of the subject comprises inserting the radiation source into a tumor inside the body of the subject.

17. The method according to claim 15, wherein inserting the radiation source into the body of the subject comprises inserting the radiation source such that the radiation source is within 0.1 mm of a tumor inside the body of the subject.

18. The method according to claim 15, wherein the thickness of the layer of the polymer is between 0.1 micron and 2 microns.

19. The apparatus according to claim 1, wherein the thickness of the layer of the polymer is between 0.1 micron and 1 micron.

20. The apparatus according to claim 1, wherein the polymer comprises Polydimethylsiloxane (PDMS).

* * * * *